United States Patent [19]

Ehrenpreis et al.

[11] 4,439,452

[45] Mar. 27, 1984

[54] CLASS OF ANALGESICS AND/OR ANTI-INFLAMMATORY AGENTS CONSISTING OF INHIBITORS OF BREAKDOWN OF ENDOGENOUS ENKEPHALIN AND/OR ENDORPHIN, AND COMBINATIONS OF SAID ANALGESICS WITH ANTIPYRETIC, ANTI-INFLAMMATORY (ASPIRIN-TYPE) DRUGS

[75] Inventors: Seymour Ehrenpreis, 4339 Birchwood Ave., Skokie, Ill. 60076; Joseph E. Comaty, Des Plaines; Reuben C. Balagot, Chicago, both of Ill.

[73] Assignee: Seymour Enrenpreis, Skokie, Ill.

[21] Appl. No.: 75,663

[22] Filed: Sep. 14, 1979

Related U.S. Application Data

[63] Continuation-in-part of Ser. No. 12,043, Feb. 14, 1979, abandoned, which is a continuation-in-part of Ser. No. 882,975, Mar. 3, 1978, abandoned.

[51] Int. Cl.³ ................. A61K 31/195; A61K 31/615
[52] U.S. Cl. ..................................... 424/319; 424/233
[58] Field of Search ................................ 424/319, 233

[56] References Cited

PUBLICATIONS

Merck Index, (1960), 7th Ed. p. 800.
Chem. Abst., 8th Coll. Index (1973), p. 17430s, "Indene–Livei".

Primary Examiner—Stanley J. Friedman
Attorney, Agent, or Firm—Norman Lettvin

[57] ABSTRACT

A new class of analgesics is provided by substances that inhibit breakdown of endogenous substance such as enkephalins and/or endorphins. The analgesic effect of an enkephalin breakdown inhibitor is greatly enhanced by being combined with an antipyretic, anti-inflammatory analgesic, herein designated as an aspirin-type drug. Specifically, both D-phenylalanine and D-leucine, each an enkephalin breakdown inhibitor, when used separately provides excellent analgesia in animals and man without developing tolerance or addiction in either species. Use of a combination of D-phenylalanine and D-leucine provides a greatly enhanced analgesia approaching the analgesia achieved by morphine. Analgesia by the latter combination is very long-lasting in animals. The injection of a combination of D-phenylalanine and an aspirin-like drug that is antipyretic and anti-inflammatory, in an animal provides a greatly enhanced analgesia approaching the analgesia achieved by morphine. Analgesia by D-phenylalanine is very long-lasting in humans. D-phyenylalanine also exhibits anti-inflammatory character, as demonstrated in animal tests.

14 Claims, No Drawings

CLASS OF ANALGESICS AND/OR ANTI-INFLAMMATORY AGENTS CONSISTING OF INHIBITORS OF BREAKDOWN OF ENDOGENOUS ENKEPHALIN AND/OR ENDORPHIN, AND COMBINATIONS OF SAID ANALGESICS WITH ANTIPYRETIC, ANTI-INFLAMMATORY (ASPIRIN-TYPE) DRUGS

This Application is a continuation-in-part of copending application, Serial No. 12,043, filed Feb. 14, 1979, which in turn was a continuation-in-part of Serial No. 882,975 filed Mar. 3, 1978, both are now abandoned.

FIELD OF THE INVENTION

This invention relates to analgesia. More particularly, this invention relates to a treatment of animals and humans by the administering of a substance that inhibits and/or delays the inherent breakdown of a class of naturally occurring analgesics that are created and exist within animals.

BACKGROUND OF THE INVENTION

Enkephalins and endorphins are morphine-like substances which have recently been discovered to be endogenous in various animal species, including mammals and man. Enkephalins and endorphins are peptides and/or polypeptides. Enkephalins are normally present in the brain.

It has heretofore been observed that enkephalins and endorphins have an ability to act as analgesics, to abolish pain, when administered to various animals by certain special routes (e.g. directly into the brain) that pose practical drawbacks to useful administration. These substances have a drawback that they are addicting, and tolerance develops to them. They have an additional drawback of having an effect of very short duration of action, due to their rapid destruction by other substances endogenous to animal species, including mammals and man. These endogenous substances that destroy the action of enkephalins include at least two known enzymes, carboxypeptidase A and leucine aminopeptidase.

D-phenylalanine and DL-phenylalanine are known chemicals listed in the Merck Index.

Use of phenylalanine has been reported from the Faculty of Medicine, Buenos Aires, Argentina in "Therapy of Depression of Phenylalanine", Arzneim Forsch, Vol. 25, NR1 (1975), and "Use of D-Phenylalanine In Parkinson's Disease," Arzneim Forsch, Vol. 26, NR4 (1976). In the report on treatment of depression, DL-phenylalanine was administered in quantity of 50 or 100 mg. per day for 15 days, and D-phenylalanine was administered in quantity of 100 mg. per day for 15 days.

A commercial drug, sold under the Trademark "Deprenon", is available for treatment of depression, by oral ingestion of 3-4 capsules per day. Deprenon's specifications state that each capsul contains:

| D-phenylalanine | 50 mg. |
| Manitol | 90 mg. |
| Pervidone | 4 mg. |
| Magnesium Stearate | 3 mg. |

BRIEF SUMMARY OF THE INVENTION

It is herein postulated that since enkephalins are endogenous, but after being formed and released for effecting endogenous analgesia, they are then rapidly destroyed by other endogenous substances, it might be possible to secure a longer lasting, or prolonged, endogenous analgesic effect if the said endogenous destruction of the endogenous analgesic substance can be inhibited and/or delayed.

One object of this invention is to provide a safe and practical method of securing in mammals a long lasting, or prolonged, endogenous analgesic effect from naturally occurring enkephalins and/or endorphins.

In testing certain substances to serve as inhibitors of the endogenous destruction of enkephalins, it has been discovered that by virtue of such actions, certain of such inhibitors operate by such a mechanism to abolish pain.

The substances discovered constitute an entirely new class of analgesics. The most potent substance tested thus far is D-phenylalanine. Another substance with a significant effect is hydrocinnamic acid. It is presently anticipated that leucyl valine may also prove to have a significant effect.

Another substance with a very significant effect is D-leucine. The combination of D-phenylalanine and D-leucine has proven to result in a potentiation of the analgesic activity of either substance used alone. The chronic administration of the combination of D-phenylalanine and D-leucine has produced very long-lasting analgesia in mice. Each of the foregoing substances is available in a powder form and is water soluble.

DL-phenylalanine (a mixture of D-phenylalanine and L-phenylalanine) and DL-leucine (a mixture of D-leucine and L-leucine) may be economically used, respectively, as a source of D-phenylalanine and D-leucine whose utility is disclosed herein. The DL-form of those two chemicals is less expensive than the pure D-form of those two amino acids.

The analgesic characteristics of the new class of substances were determined by examining animal reaction to a single treatment, referred to as an "acute" experiment or test, and also to prolonged administration, referred to as a "chronic" experiment or test, to determine if tolerance develops.

It has also been postulated that the analgesic effect of the new class of substances might be enhanced or potentiated by combining the substance with an antipyretic, anti-inflammatory analgesic, which is commonly referred to as an aspirin-type drug. The theory in support of this postulate is that such aspirin-type drugs are known inhibitors of various enzymes, particularly prostaglandin synthetase. It has also been observed that aspirin-type drugs may enhance, or potentiate, the action of narcotic analgesics, and such drugs have been used in such combinations of ingredients as: codeine and aspirin, and Darvon and aspirin.

Thus, another object of this invention is to provide a new combination of analgesic materials in which the analgesic effect of the substances of the combination will be greatly potentiated over the analgesic effect attained when each substance is considered separately, thereby achieving a synergistic effect approaching the analgesic effect of morphine.

Further objects and advantages will become apparent to one skilled in the art as the description of this invention proceeds.

The results of the acute tests, or experiments, are reflected in Tables 1 and 2 set out hereinafter in section "A". The chronic tests and experiments are described in section "B" hereinafter. The results of acute tests, or experiments, using a combination of substances is reflected in Table 3 of section "C" set out hereinafter.

D-phenylalanine in pure form, or as part of DL-phenylalanine, has been administered to 47 humans with both acute (4) and chronic (43) pain. Analgesia has been obtained in at least 28 (60%) of the subjects.

A. General Description Of Acute Tests Of Individual Substances, And Effect Of The Substances Tested The tests herein described were intended to establish at least one safe and practical method of securing in animal species, such as mammals, a long lasting, or prolonged, analgesic effect from the enkephalins, and possibly of the endorphins, naturally occurring in the animal.

One test for the ability of the animal to withstand pain is the hot-plate test. It is a traditional pharmacological screening procedure in which drug-treated mice are placed on a hot plate and the analgesic effect of the drug is measured by how soon a mouse jumps off the hot plate. In the specific hot-plate test described herein the temperature of the plate was maintained at 55° C.

Another test for the ability of the animal to withstand pain is the phenylquinone writhing test. Phenylquinone, when injected into mammals such as mice causes intense pain manifested by stretching, pelvic twisting, and extension of hind legs. An analgesic such as morphine, when administered to the mouse, will either abolish or reduce the number of such reactions to phenylquinone, the totality of response being known as writhing.

The practical method of administering the inhibitor or analgesic substances herein described in mice was by intraperitoneal injection. The dosage injected was 250 mg/kg, the dosage being proportional to the weight of the mouse treated.

The "control" for the hot-plate test is determined by placing an untreated mouse on a metal hot plate maintained at 55° C. The time it takes the untreated or "control" mouse to jump, after being placed on the hot plate, is noted. After being treated by an intraperitoneal injection, the mouse is again placed on the hot plate, and the lapse of time until the animal jumps is noted. This test of a treated mouse is repeated at various specified times. Specifically, the mouse is tested after a single injection for 2 hours at 30-minute intervals. In the experiments with mice, six to twelve mice were tested with each dose of injected substance. A "highly significant" analgesic effect will be demonstrated by a time lapse, before the mouse jumps, constituting an increase of several-fold (3 or 4) over that of the control.

In the writhing test, the analgesic injected is administered to certain mice approximately one hour before injecting the phenylquinone. Other animals serving as a "control" are injected with saline solution approximately one hour before injecting the phenylquinone. The percent of animals writhing, together with the number of writhes is noted over a period of 10 minutes following injection of the phenylquinone.

The human studies noted herein were carried out on 47 subjects experiencing acute and chronic pain which had not been relieved by conventional treatment with drugs or other procedures such as acupuncture, transcutaneous nerve stimulation, or laminectomy. D-phenylalanine plus aspirin, D-phenylalanine alone, or DL-phenylalanine were administered orally and the degree of relief from pain was monitored for a period of several weeks.

The results of all tests were subjected to statistical analysis to determine the degree of significance of results.

Effect Of The Substances Tested

D-phenylalanine and hydrocinnamic acid both exhibited highly significant analgesia by the hot-plate test. This conclusion is supported by the data shown in Table 1. With injection of a saline solution, as a control, no significant increase in jump time was observed or noted. With injection of D-phenylalanine or hydrocinnamic acid, a highly significant increase in time lapse before jump was observed.

TABLE 1

Analgesic Potency of Inhibitors of Enkephalin Breakdown, As Determined by the Hot Plate Method.

| Treatment (Injection) | % Increase in Jumping Time |
|---|---|
| Saline | 30%** |
| D-phenylalanine | 300%* |
| L-phenylalanine | 30%** |
| Hydrocinnamic acid | 300%* |

*Highly significant
**Not significant

Specificity of D-phenylalanine as an inhibitor substance is determined by comparison of results from its injection with results from injection of L-phenylalanine, a natural occurring amino acid, whose testing showed minimal, if any, significant analgesic potency. It is known that L-phenylalanine is a poor inhibitor of carboxypeptidase A. Naloxone exhibits the ability to reverse analgesia produced by D-phenylalanine. Since naloxone is a highly specific antagonist of morphine and the endorphins, this effect of naloxone supports the theory that D-phenylalanine may be producing analgesia by a mechanism involving the endorphins.

Table 2 shows that injection of D-phenylalanine also significantly decreased the number of test animals showing writhing. Reduction in intensity of writhing is shown by the reduction in number of writhes per minute. Table 2 again shows that injection of L-phenylalanine has relatively little effect.

TABLE 2

Analgesic Potency of Inhibitors of Enkephalin Breakdown, As Determined by the Phenylquinone Writhing Test

| Treatment (Injection) | % Writhing | Number of Writhes/Minute |
|---|---|---|
| Saline | 90% | 5.4 |
| D-phenylalanine | 60% | 2.5* |
| L-phenylalanine | 80% | 4.4** |

*Highly significant
**Not significant

Results using D-leucine in the hot plate and writhing tests are shown in the following Table 3. Just as in the case of D-phenylalanine, analgesia by D-leucine was reversed by naloxone. Results are also shown for the combination of D-phenylalanine and D-leucine in these tests. Such results show the potentiation of action by the combination of these amino acids.

TABLE 3

Analgesic Potency of D-Leucine and D-Leucine Plus D-Phenylalanine as Determined by the Hot Plate and Phenylquinone Writhing Tests

| Treatment (Injection) | Hot Plate % Increase in Jumping Time | Writhing Test # of Writhes per Minute |
|---|---|---|
| Saline | — | 5.6 |
| D-leucine, 250 mg/kg | 300* | 3.0* |
| D-leucine, 125 mg/kg + D-phenylalanine, 125 mg/kg | 300* | — |
| D-leucine, 250 mg/kg + D-phenylalanine, 250 mg/kg | — | 1.0* |

*Highly significant

B. Chronic Experiments

D-phenylalanine was injected intraperitoneally, twice daily for nine (9) days, into mice, in an amount per injection of 250 mg per kg weight of the mouse. All animals were tested by the hot-plate test on the ninth day for appearance of analgesia, both before the injection of the phenylalanine as well as afterwards. Two types of controls were also run. One control group of mice was injected with saline solution; the other group was injected with L-phenylalanine. Twenty animals were used for each of the three groups.

After administration of the second dose of phenylalanine on the ninth day, the animals that had been injected with D-phenylalanine were injected with naloxone, 20 mg/kg. Naloxone is an antagonist of morphine. The purpose of this latter test was to test for withdrawal symptoms, because with opiate-dependent animals, the amount of injected naloxone will produce severe withdrawal symptoms including diarrhea, large weight loss, and jumping.

The following results were observed in the mice that had been injected with D-phenylalanine for nine (9) days.

(a) Tolerance to the analgesic effects did not develop. In other words, the degree of analgesia in the D-phenylalanine injected mice, as measured by the hot-plate test, on the ninth day was essentially the same as that observed on the first day. If morphine, or other opiate substance, had been administered in a similar fashion, by the ninth day the administration of morphine, in the same amount as administered on the first day would have had very little analgesic effect, the latter result being a reflection of tolerance.

(b) There seems to be a cumulative effect from the repeated injections, over an extended period of time, of D-phenylalanine (i.e., excellent analgesia to the hot-plate test was observed in the mice as long as 12 hours after the last dose had been injected.)

(c) The control group of mice injected with saline solution or with L-phenylalanine exhibited virtually no analgesia.

The following results were observed, after naloxone injection, in mice that had been injected with D-phenylalanine for nine (9) days:

(d) No sign of addiction was observed from administration of the naloxone test: (i.e. there was no diarrhea, weight loss, jumping, etc.)

(e) Naloxone only abolished the analgesia. (This was to have been expected if analgesia is indeed due to involvement of enkephalin and/or endorphin in the process.)

The foregoing results from several tests demonstrate the efficacy of using inhibitors of enkephalin breakdown as analgesics. The substances are effective, do not produce tolerance or dependence, and are extremely safe. Even at very high doses of DPA given over an intended period of time, no deaths or tissue pathology were observed in any of the experimental animals. On the basis of the animal experiments, it was anticipated that either D-phenylalanine, or some other equivalent, such as a more potent inhibitor of breakdown of enkephalins, would be extremely useful as an analgesic in man.

The degree of analgesia obtained with D-phenylalanine is not, initially, as intense as that secured by use of morphine and other narcotic analgesics. However, it is conceivable that more potent inhibitors of enkephalin and/or endorphin breakdown might prove to be at least equivalent, and perhaps even more effective, analgesics than D-phenylalanine.

It is considered that the analgesia produced by the combination of D-phenylalanine and D-leucine is equivalent to that obtained with fairly large doses of morphine (15 to 20 mg/kg).

C. Combinations Of Enkephalin Breakdown Inhibitors With Antipyretic-Analgesic (Aspirin-Type) Drugs It has been discovered that the analgesia produced by enkephalin breakdown inhibitors, such as D-phenylalanine, can be greatly enhanced, or potentiated, by having an anti-inflammatory, antipyretic drug combined therewith. Such anti-pyretic, anti-inflammatory agents may include aspirin, indo-methacin, diclofenac sodium, ibuprofen also known by trademark "Motrin", tolmetin sodium also known by trademark "Tolectin", naproxen also known by trademark "Naprosyn" and equivalents. Such antipyretic-analgesics are commonly referred to as aspirin-type drugs. Such drugs themselves are inhibitors of various enzymes, particularly prostaglandin synthetase. Significantly, the hot-plate test reflects that injection of indomethacin or diclofenac sodium at a dose which failed to provide a significant increase in jumping time of a mouse, when combined with D-phenylalanine provided an unusually highly effective analgesia as is reflected in Table 4. Prior to the invention herein, it could not have been predicted that such a combination would provide such an unusual effect. In fact, the analgesia obtained by use of the combination of substances approached that analgesia obtained by one of the most potent known analgesics, morphine.

For combination experiments involving D-phenylalanine and the aspirin-like synthetase inhibitors, the following procedure was used: A series of mice were first administered either indomethacin or diclofenac sodium. At various times, the animals were tested by the hot-plate method. After one hour, D-phenylalanine was administered at a dose of 250 mg/kg and the animals were tested for analgesia for another two hours. The results are shown in Table 4. When D-phenylalanine was administered to mice which had previously been treated with a synthetase inhibitor, the effect of the combination was to increase the jumping time 1100 or 1200%, i.e., eleven or twelvefold. In some instances, the increase was at the maximum equivalent to that of morphine or other narcotic analgesics. It will be recalled from Table 1 above that the same dose of D-phenylalanine caused an increase in jumping time of only 300%, while as shown in Table 4 that of the synthetase inhibitors gave essentially no analgesia. Thus, the results from the combination of the two substances represent a true synergism, or example of drug potentiation.

TABLE 4

Analgesic Potency of Combinations of D-phenylalanine and Indomethacin or Diclofenac Sodium.

| Treatment | % Increase in Jumping Time |
|---|---|
| D-phenylalanine, 250 mg/kg | 300 |
| Indomethacin, 20 mg/kg | 0 |
| Indomethacin, 20 mg/kg followed by D-phenylalanine, 250 mg/kg | 1100 |
| Diclofenac sodium 40 mg/kg | 33 |
| Diclofenac sodium 40 mg/kg followed by D-phenylalanine, 250 mg/kg | 1200 |

Preliminary experiments in treatment of pain in human subjects using D-phenylalanine, D-phenylalanine plus aspirin, or DL-phenylalanine, by oral route shows that the efficacy of these substances as analgesics in man has been confirmed. As shown in Table 5 which lists representative results, long lasting pain relief can be achieved with any of the above chemicals given for 3 or 4 days. No side effects, tolerance, or signs of addiction were observed in any patient.

Preliminary success in experiments in treatment of pain in human subjects was also achieved by using D-leucine.

The anticipated preferred range of administration of D-phenylalanine is 100–750 mg. dosage, taken four times per day, or a total of 400–3,000 mg. per day. When said preferred range of dosage is administered with aspirin, the aspirin component will be at a fixed rate of 300 mg. per dosage.

It has now been determined by experimentation with animals that D-phenylalanine exhibits anti-inflammatory character. Information re such tests is as follows: Rat paw carageenan test for anti-inflammatory action of DPA: This is a standard test for determining whether a drug can act as an anti-inflammatory agent in man. Carageenan is a highly irritating substance and causes swelling of tissues when injected. An anti-inflammatory agent is one which can counteract such swelling. A convenient tissue for accurately measuring degree of swelling is the hind paw of the rat which swells up greatly when the carageenan is injected. The degree of swelling is easily measured by immersing the paw in water and noting the degree of fluid displacement. In the experiments carried out, DPA was administered either orally or intraperitoneally 2–3 hours before the carageenan. The effect of DPA was compared with that of control paws of animals administered saline instead of DPA.

TABLE 5

D-Phenylalanine (DPA) Analgesia In Humans

| CONDITION | DURATION | PRIOR TREATMENT | TIME ON DPA | RESULT |
|---|---|---|---|---|
| Whiplash | 2 years | Empirin, Valium | 3 days | Complete relief, 1 month |
| Osteoarthritis, fingers, thumbs of both hands | 5 years | Empirin, aspirin | Maintained | Excellent relief; joint stiffness reduced |
| Rheumatoid arthritis (left knee), osteoarthritis of hands | Several years | Empirin + codeine | 1 week | Considerable relief |
| Low back pain, neck pain | Several years | 90 acupunctures | 3 days | Low back pain gone walked one mile |
| Low back pain | Several years | Spinal fusion, percutaneous nerve stimulation | 3 days | Much less pain |
| Low back pain | Several years | Laminectomies, Depomedrol, percutaneous nerve stimulation | 3 days | Good to excellent relief |
| Fibrositis of muscle | * | Empirin | 3 days | Pain gone, recurred after 2 days |
| Migraine headache | Several years | * | 2 days | Good relief, may prevent recurrence |
| Cervical osteoarthritis plus post-operative pain | * | * | 2 days | Very little pain |
| Severe lower back pain | Several years (intermittent) | Empirin, Valium | 3 days | Excellent relief |

*means information not available

In the treatment of pain in human subjects, reported in Table 5, the dosage of D-phenylalanine administered was in the range of 800–1,000 mg. per day, administered in 4 equal installments of 200–250 mg. per dosage. These amounts had been selected conservatively. When administration was with aspirin, 300 mg. aspirin was added to the D-phenylalanine.

When DL-phenylalanine was administered, the installments were of double weight, on the assumption that the D-phenylalanine component of the DL-phenylalanine was 50%.

TABLE

Activity of D-Phenylalanine in Rat Paw Carageenan Test

| Dose of DPA mg/kg | Route of Administration | Time before carageenan, minutes | % Inhibition Swelling |
|---|---|---|---|
| 1000 | i.p. | 120 | −71 |
| 500 | i.p. | 120 | −59 |
| 250 | i.p. | 120 | −61 |
| 125 | i.p. | 120 | −61 |
| 1000 | oral | 180 | −30 |
| 500 | oral | 180 | −42 |
| 250 | oral | 180 | −35 |
| 125 | oral | 180 | −38 |

In view of the results obtained by experimentation with D-leucine, DL-phenylalanine, and DL-leucine, and by mixtures of same, and by combination of such D isomers, known as D optical isomers of amino acids, with antipyretic, anti-inflammatory agents of the aspirin-type, the latter yielding synergistic effect, it is anticipated and therefore predicted, without present experimentation, that methods of use of same in humans and compositions will result in advantages as previously secured in connection with treatment for relief of pain.

What is claimed and desired to be secured by Letters Patent of the United States is:

1. A method for effecting anti-inflammatory relief in animals or humans by the step of administering to the animal or human suffering inflammation a substance intended to inhibit the destruction of endogenous substances such as enkephalins and endorphins, the substance administered being D-phenylalanine in an effective amount for effecting anti-inflammatory relief.

2. A method for effecting anti-inflammatory relief in animals or humans by the step of administering to the animal or human suffering inflammation a substance intended to inhibit the destruction of endogenous substances such as enkephalins and endorphins, the substance administered being a particular form of an amino acid, namely the D optical isomer of the amino acid, in an effective amount, for providing anti-inflammatory relief, selected from a group of amino acids that consists of at least phenylalanine and leucine.

3. A method as in claim 1 wherein the substance administered is an effective amount of a combination of amino acids selected from a group that consists of D-phenylalanine, D-leucine, DL-phenylalanine, and DL-leucine.

4. A method for effecting relief of pain in animals or humans by the step of administering to an animal or human having pain a substance intended to inhibit the destruction of endogenous substances such as enkephalins and endorphins, the substance administered being D-phenylalanine in an analgesically effective amount.

5. A method for effecting relief of pain in animals or humans by the step of administering to an animal or human having pain a substance intended to inhibit the destruction of endogenous substances such as enkephalins and endorphins, the substance administered being a particular form of an amino acid, namely the D optical isomer of the amino acid, in an analgesically effective amount, selected from a group of amino acids that consists of phenylalanine and leucine.

6. A method as in claim 4 or claim 5 wherein the administration of said substance is accompanied by substantially simultaneous administration of an effective amount of an antipyretic, anti-inflammatory, agent of the aspirin-type.

7. A method as in claim 4 or claim 5 wherein the relief of pain is effected in humans by oral administration of the substance.

8. A method as in claim 4 or claim 5 wherein the D-phenylalanine is administered to humans orally in an amount of at least 400 mg. per day.

9. A method as in claim 4 or claim 5 wherein the substance is administered to humans orally in an amount in the range of 400–3000 mg. per day.

10. A method as in claim 4 or claim 5 wherein the administration of the analgesically effective amount of substance is in substantially equal doses of about 4 per day.

11. A method as in claim 4 wherein the substance administered is DL-phenylalanine.

12. A method for effecting relief of pain in animals or humans by the step of administering to an animal or human having pain a substance intended for inhibiting the destruction of endogenous substances such as enkephalins and endorphins, the substance administered being an analgesically effective combined amount of amino acids selected from a group that consists of D-phenylalanine, D-leucine, DL-phenylalanine, and DL-leucine.

13. A method as in claim 12 wherein the substance administered is a combination of D-phenylalanine and D-leucine.

14. A composition, for the treatment of animals or humans suffering from pain or inflammation, consisting of an analgesically effective combined amount of two or more amino acids selected from a group of amino acids that consists of D-phenylalanine, D-leucine, DL-phenylalanine, and DL-leucine.

* * * * *